(12) United States Patent
Guenther

(10) Patent No.: US 10,006,839 B2
(45) Date of Patent: Jun. 26, 2018

(54) METHOD FOR FLATTENING SAMPLE IN OPTICAL METROLOGY

(71) Applicant: Bryan Guenther, Tucson, AZ (US)

(72) Inventor: Bryan Guenther, Tucson, AZ (US)

(73) Assignee: BRUKER NANO, INC., Santa Barbara, CA (US)

( * ) Notice: Subject to any disclaimer, the term of this patent is extended or adjusted under 35 U.S.C. 154(b) by 372 days.

(21) Appl. No.: 15/060,385

(22) Filed: Mar. 3, 2016

(65) Prior Publication Data

US 2016/0187234 A1 Jun. 30, 2016

Related U.S. Application Data

(62) Division of application No. 13/798,865, filed on Mar. 13, 2013, now Pat. No. 9,303,631.

(51) Int. Cl.
| | |
|---|---|
| *B30B 1/38* | (2006.01) |
| *G01N 1/28* | (2006.01) |
| *F04B 37/10* | (2006.01) |
| *F04B 53/14* | (2006.01) |
| *G01B 9/02* | (2006.01) |
| *G03B 27/20* | (2006.01) |
| *B30B 1/00* | (2006.01) |
| *G01B 9/00* | (2006.01) |

(52) U.S. Cl.
CPC .............. *G01N 1/286* (2013.01); *B30B 1/007* (2013.01); *B30B 1/38* (2013.01); *F04B 37/10* (2013.01); *F04B 53/14* (2013.01); *G01B 9/00* (2013.01); *G01B 9/02* (2013.01); *G03B 27/20* (2013.01)

(58) Field of Classification Search
CPC .......... B30B 1/38; B30B 1/007; G01N 1/286; G01B 9/00; G01B 9/02; F04B 7/00; F04B 37/10; F04B 53/14; H01L 31/0232; G03B 27/20; G02B 26/001; G02B 1/06; B32P 37/1009; B32P 37/1018; B65F 1/127
USPC ... 100/90, 219, 266, 269.01, 269.05, 269.11, 100/269.13
See application file for complete search history.

(56) References Cited

U.S. PATENT DOCUMENTS

| | | | | | |
|---|---|---|---|---|---|
| 2,174,882 | A | * | 10/1939 | Huebner ............... | G03B 27/20 101/DIG. 36 |
| 3,591,285 | A | * | 7/1971 | Hakogi .................. | G03B 27/20 101/32 |
| 4,054,383 | A | * | 10/1977 | Lin ........................ | G03B 27/20 101/389.1 |
| 4,080,068 | A | * | 3/1978 | Madigan ............... | G03B 27/66 355/71 |
| 4,696,227 | A | * | 9/1987 | Van Buskirk ........... | B30B 1/00 100/245 |

(Continued)

*Primary Examiner* — Jimmy T Nguyen

(74) *Attorney, Agent, or Firm* — Antonio R. Durando

(57) ABSTRACT

A vacuum mechanism for flattening bowed panel samples includes a support structure with coplanar support elements and a fixture with a movable component actuated by a vacuum source. The movable component has a top surface disposed above the support elements when no vacuum is applied and is capable of being drawn to a substantially coplanar position with the support elements when actuated by the vacuum source. The top surface is fluidly connected to the vacuum source and adapted to adhere to the overlaying surface of the sample when vacuum is applied, thereby flattening the sample when the movable component is drawn in by the same vacuum source.

9 Claims, 7 Drawing Sheets

(56) References Cited

U.S. PATENT DOCUMENTS

| | | | | |
|---|---|---|---|---|
| 5,144,365 A | * | 9/1992 | Visage | G03B 27/20 |
| | | | | 355/91 |
| 5,501,144 A | * | 3/1996 | Bryson | A47J 43/286 |
| | | | | 100/116 |
| 5,818,035 A | * | 10/1998 | Krivanek | H01L 31/0203 |
| | | | | 250/208.1 |
| 9,303,631 B1 | * | 4/2016 | Guenther | B30B 1/38 |
| 2011/0033620 A1 | * | 2/2011 | Polyak | C23C 16/4586 |
| | | | | 427/248.1 |

* cited by examiner ated by the vacuum source. The movable component has a top surface disposed above the support elements when no
METHOD FOR FLATTENING SAMPLE IN OPTICAL METROLOGY

RELATED APPLICATIONS

This application is a divisional application and claims the priority of U.S. Ser. No. 13/798,865, filed Mar. 13, 2013, now U.S. Pat. No. 9,303,631.

BACKGROUND OF THE INVENTION

Field of the Invention

This invention pertains to the general field of optical metrology. In particular, it pertains to a fixture for flattening large samples being measured with an optical instrument such as an interferometer.

Description of the Prior Art

When measuring a relatively large sample such as a flexible circuit-board panel with an optical instrument, it is very desirable to hold the panel as flat as possible. Such samples are measured at a plurality of locations distributed over the surface of the panel and each measurement is preceded by a focusing procedure whereby the objective of the instrument is placed at a best-focus position prior to capturing the optical information constituting the measurement. Therefore, a perfectly flat sample greatly reduces the time required to focus the objective on the sample surface.

Various mechanisms have been used in the art in order to flatten large, flexible, panel-like samples. The typical sample stage consists of a platform over which the sample rests during the measurement, normally clamped at the edges to keep it in place under conditions that minimize contact of its bottom surface with the support structure. When the sample is bowed downward producing a lower convex surface, it can be flattened by a simple mechanical support that keeps the center of the sample roughly coplanar with the outer edges. Such a mechanism could be, for example, a thin and rigid cross-like structure over which the sample bears when clamped to the stage. When the sample is bowed upward, however, its center cannot be brought down from the top without significant interference from the actuating mechanism, which is cumbersome and undesirable.

Vacuum devices are known in the art for flattening large samples by drawing them to a flat support platter so as to conform to its surface. Channels in the platter provide the means by which the vacuum is exerted on the sample after it contacts the platter. However, these devices are unsuitable for circuit boards that require a minimum amount of contact with the flattening fixture and only with particular materials, such as Teflon® (PTFE—polytetrafluoroethylene) and other plastic or "non-marring" materials, that have been found not to produce damage on contact. This invention describes a suction device that flattens upwardly bowed samples with minimum contact and no damage to the bottom surface of the sample.

BRIEF SUMMARY OF THE INVENTION

The main aspect of the invention lies in the concept of simultaneously applying suction to the surface of a bowed panel sample in order to adhere a movable mechanism to it and at the same time using the same source of suction to actuate the mechanism to flatten the sample. In broad terms, the invention includes a support structure with coplanar support elements and a fixture with a movable component actuated by the vacuum source. The movable component has a top surface disposed above the support elements when no vacuum is applied and is capable of being drawn to a substantially coplanar position with the support elements when actuated by the vacuum source. The top surface is fluidly connected to the vacuum source and adapted to adhere to the overlaying surface of the sample when vacuum is applied.

In the preferred embodiment of the invention, the support structure consists of an outer frame, four coplanar beams, and a platform to support the fixture. The frame includes clamping means for retaining the bowed panel sample during the measurement. The movable component is a piston slidably connected to a housing and is urged upward by a spring-loaded mechanism limited in its maximum extension by a screw coupled to the piston. The vacuum source is fluidly connected to an interior compartment of the housing and further to the top surface of the piston through the same interior compartment of the housing. The top surface of the piston includes an O-ring.

The fluid communication with the top surface of the piston may be obtained through a single centrally located channel or multiple channels connecting it with the interior of the housing. In the latter case, indented pockets in the surface of the piston are provided around each channel to increase suction and reduce contact with the surface of the sample. In either case, the use of the O-ring may be advantageous depending on the particular sample surface.

Various other aspects and advantages of the invention will become clear from the description that follows and from the novel features particularly recited in the appended claims. Therefore, to the accomplishment of the objectives described above, this invention consists of the features hereinafter illustrated in the drawings, fully described in the detailed description of the preferred embodiments, and particularly pointed out in the claims. However, such drawings and description disclose only some of the various ways in which the invention may be practiced.

DETAILED DESCRIPTION OF THE INVENTION

The invention is a mechanism for flattening a bowed panel (or a bowed spot in a panel) so that it can be measured more rapidly with an optical profilometer. The concave lower surface of an upward bowed flexible sample clamped to the measurement stage of an optical instrument is used for simplicity of description, but the same mechanism could be used to flatten a downward bowed panel or a panel with a variety of bowed areas. The idea is to provide a double-action vacuum mechanism that contacts a small central portion of the bowed area in the surface of the sample and then flattens the area to conform to the general surface of the sample. The same vacuum source is used first to draw in the bowed area of the sample so as to cause it to adhere to a smooth non-stick piston and then to draw down the piston to a position coplanar with a support structure in the sample stage. As a result, the sample is flattened or otherwise smoothed to conform to the support fixture of the stage. The invention is described in terms of a horizontal sample stage and a lower flattening vacuum mechanism, but it is understood that it could be practiced in the same manner with any orientation of the sample stage and with any position of the mechanism that is appropriate to pull the sample toward it. For example, the stage could be positioned vertically, at an incline, or upside down with respect to the description that follows. Therefore, with regard to the scope of the invention, the claims should be interpreted with reference to a device that has been repositioned, if necessary, so as to have a horizontal sample stage with the vacuum mechanism (or mechanisms) placed as necessary to pull the sample toward it. Terms such as "above," "below," "upward" and "downward" in the claims are intended to be literal only with reference to a device after it has been so repositioned.

Figure 1:
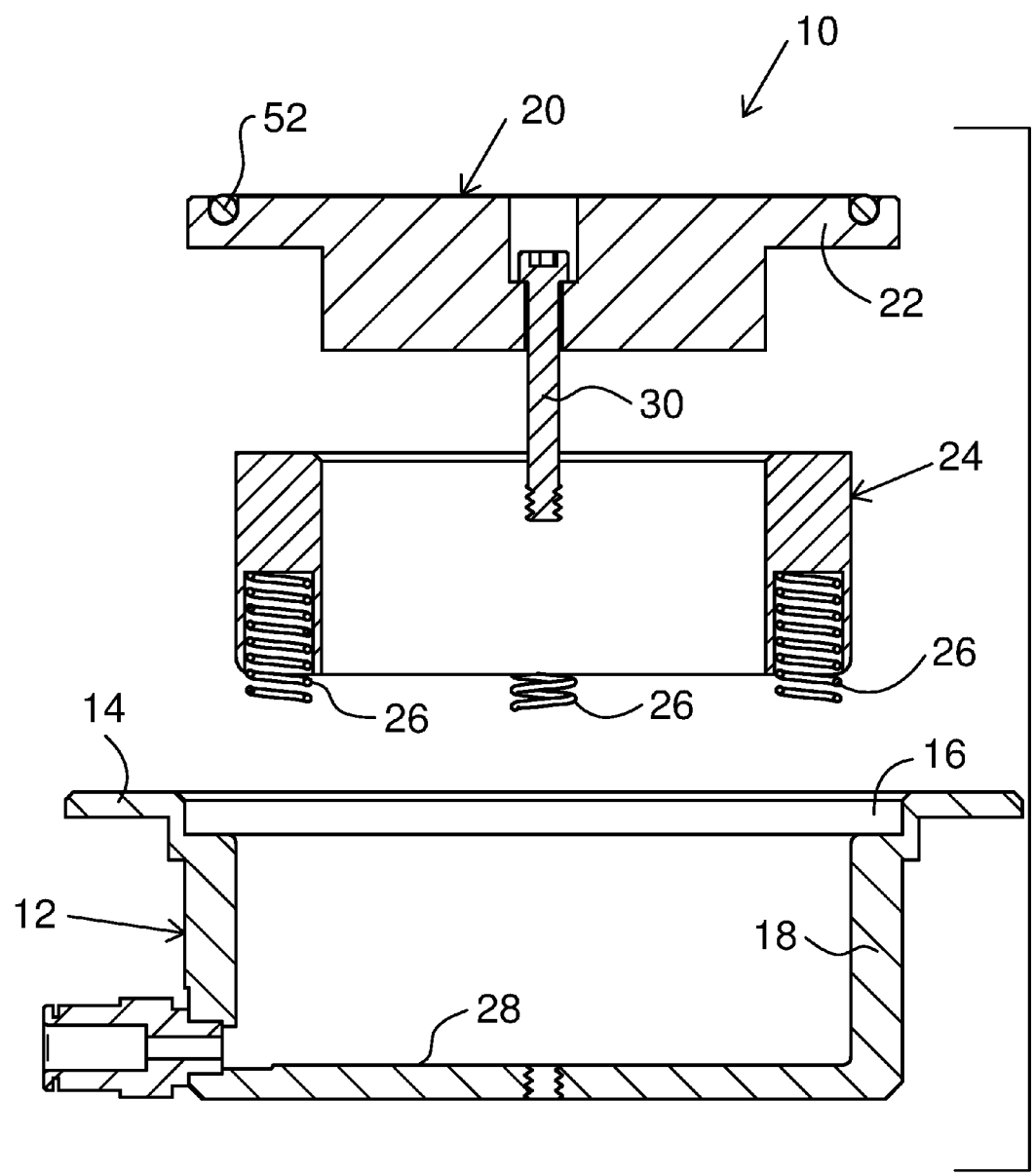
FIG. 1 illustrates in sectioned exploded view the components of a vacuum fixture according to the invention.

Referring to the figures, wherein like parts are referenced with the same numerals and symbols, FIG. 1 is an exploded view of a vacuum fixture 10 for flattening large panel samples according to the invention. The fixture comprises a cup-like housing 12, preferably cylindrical in shape, with a peripheral top rim 14 adapted to sit on a support frame (not seen in the figure) in the sample stage. An interior channel indentation 16 along the top of the wall 18 of the housing is provided to receive the flange-like outer portion of a piston 20 adapted to fit precisely into the interior of the housing 12. The flange 22 is sufficiently wide to accommodate a spring-loaded tubular sleeve 24 with springs 26 distributed evenly along the circumference of the sleeve (four are illustrated in the figures). Each spring 26 housed in the sleeve 24 is designed to bear on the inner bottom surface 28 of the housing 12 and urge the sleeve upward. Thus, as seen in the assembled view of FIG. 2, the sleeve 24 presses against the underside of the flange 22, thereby urging the piston 20 upward. A screw 30 protruding downward from the center of the piston 20 is used to assemble the fixture and compress the sleeve 24 so as to load the piston, which is preferably attached to the sleeve by means of vertical screws (not shown) inserted through the top of the piston.

Figure 2:
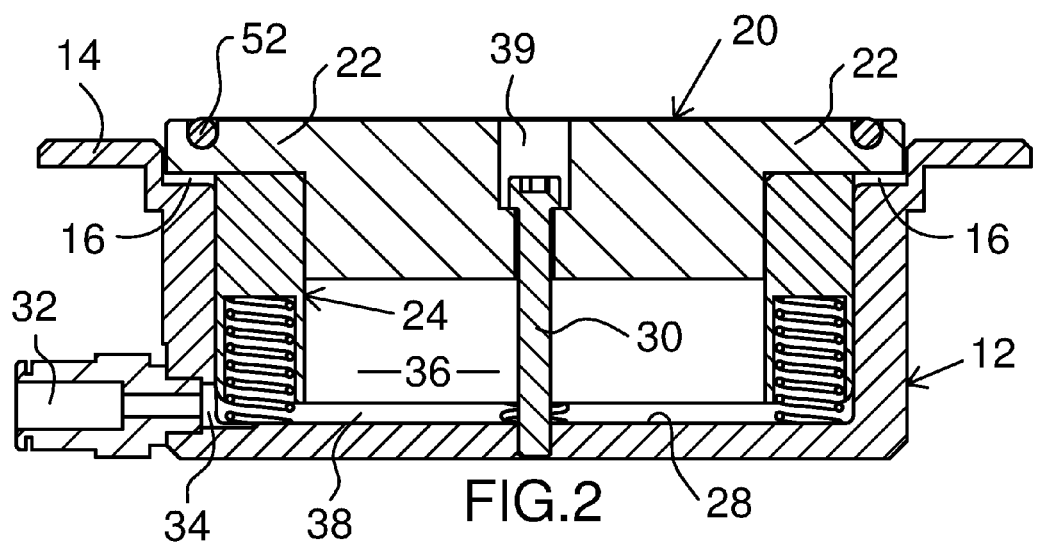
FIG. 2 illustrates in sectioned view the components of FIG. 1 assembled to produce the vacuum fixture of the invention in isolation, prior to installation on the sample stage of an optical measurement instrument.
Figure 3:
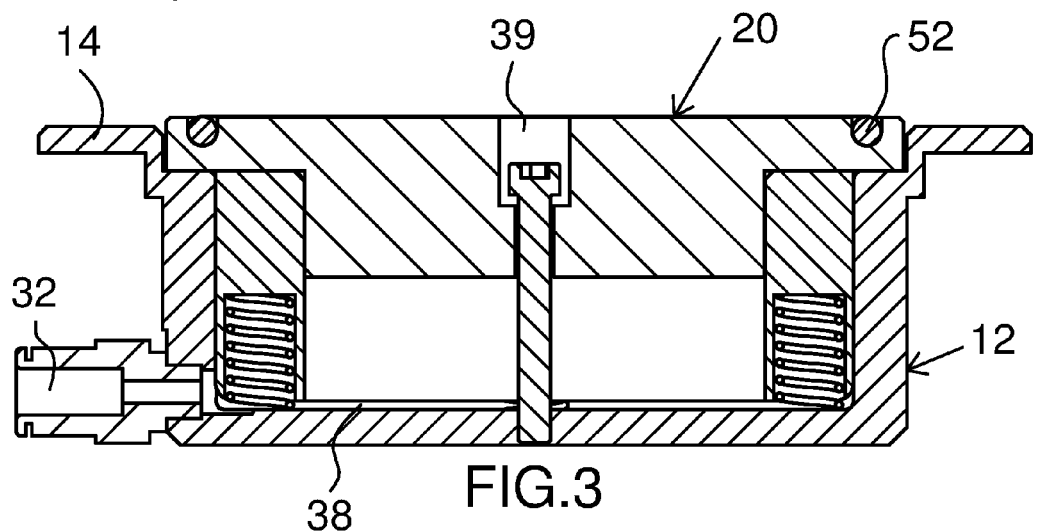
FIG. 3 illustrates the vacuum fixture of FIG. 2 in a compressed condition, when the piston is drawn all the way down to seat on the housing of the fixture.

As illustrated in FIG. 2, the position of the top surface of the piston 20 with respect to the top surface of the rim 14 is adjusted to an elevated rest position. The screw 30 is used to fine tune this position by drawing the piston downward as the screw is progressively inserted into the bottom of the housing 12 to which it is threadedly connected. Critically, the depth of the indentation 16 in the wall 18 of the housing has to be smaller than the thickness of the flange 22 in the piston, so that the top surfaces of the piston 20 lies above the rim 14 when the piston is drawn all the way down against the upward pressure of the springs 26, as illustrated in FIG. 3. This is to ensure minimum contact with the lower surface of the sample, as explained in detail below. Also critically, the fit between the sleeve 24 and the housing 12 along the interior surface of the wall 18 must be precise enough to permit relative movement with minimum friction but provide a substantially leak-proof, sealed connection. To that end, the sleeve is preferably made of brass and the abutting surfaces are machined to a precise fit. A housing 12 made of stainless steel combined with a brass sleeve 24 was found to be particularly suitable to achieve such critical fit. Brass and stainless steel can be machined to provide a close sliding fit, wear well together, and have similar coefficients of thermal expansion, thus ensuring that the fit is preserved over a wide range of temperatures.

According to the invention, a vacuum source 32 is connected to the fixture 10, such as through a channel 34 in the housing 12. The channel is connected to the interior 36 of the housing (and thus also of the fixture) via the open space 38 between the bottom of the sleeve 24 and the inner bottom surface 28 of the housing 12. In order to retain such an open space at all times, the height of the sleeve 24 is such that it does not rest on the bottom of the housing when fully compressed (as seen in FIG. 3), thereby ensuring that fluid communication with the interior of the fixture is present at all times. Finally, a channel (not shown) is provided between the screw 30 and the perforation in the piston through which the screw is passed in order to provide fluid communication also between the interior 36 of the fixture and the opening 39 in the top surface of the piston. As a result, when vacuum is applied to the fixture via the source 32, suction is exerted all the way to the opening 39. It is understood that any other perforation could be used in equivalent manner to provide fluid communication between the interior of the fixture 36 and the top surface of the piston 20.

Figure 4:
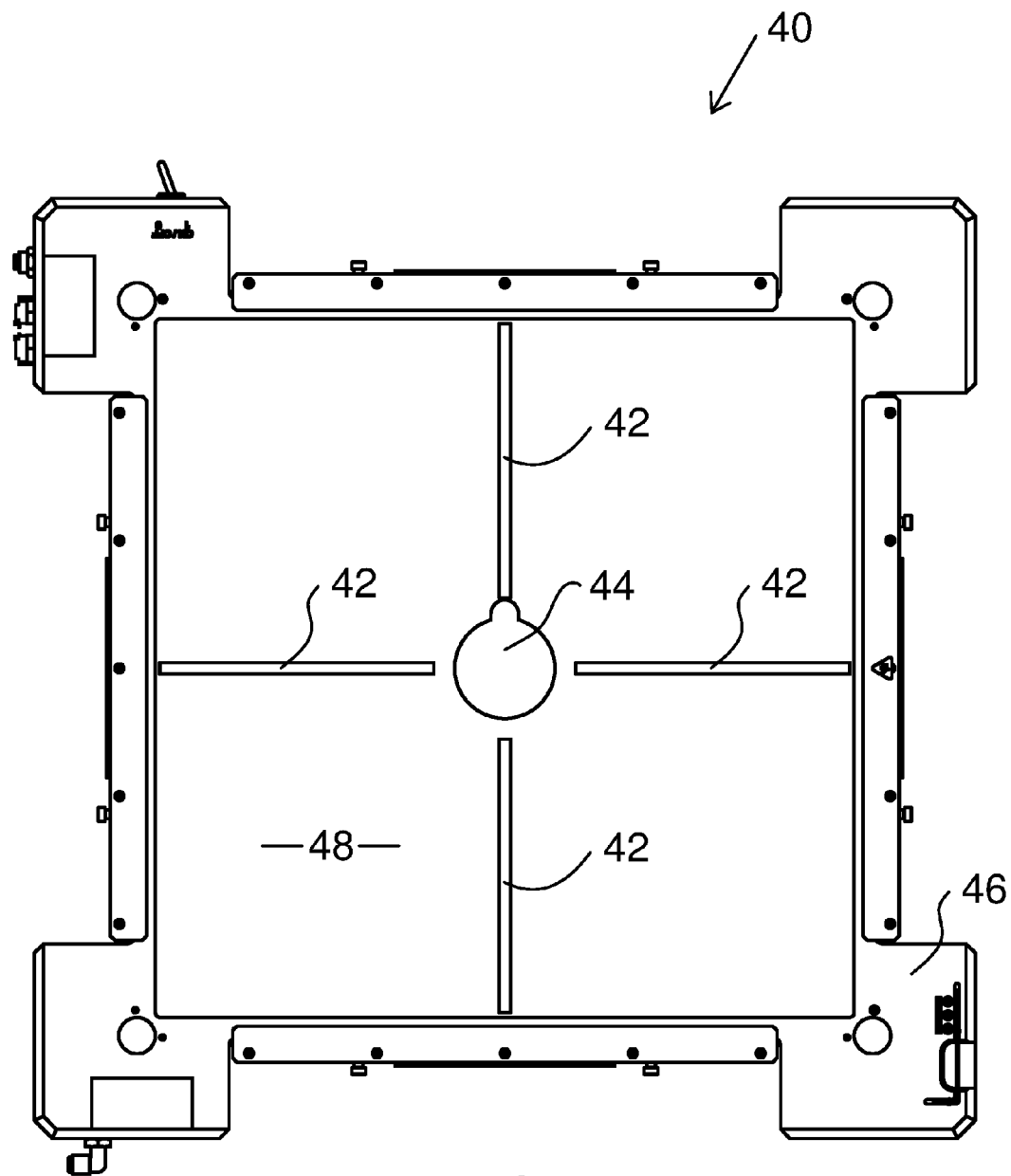
FIG. 4 is a top plan view of a support structure suitable for housing the fixture of the invention in the sample stage of an optical measurement instrument.
Figure 5:
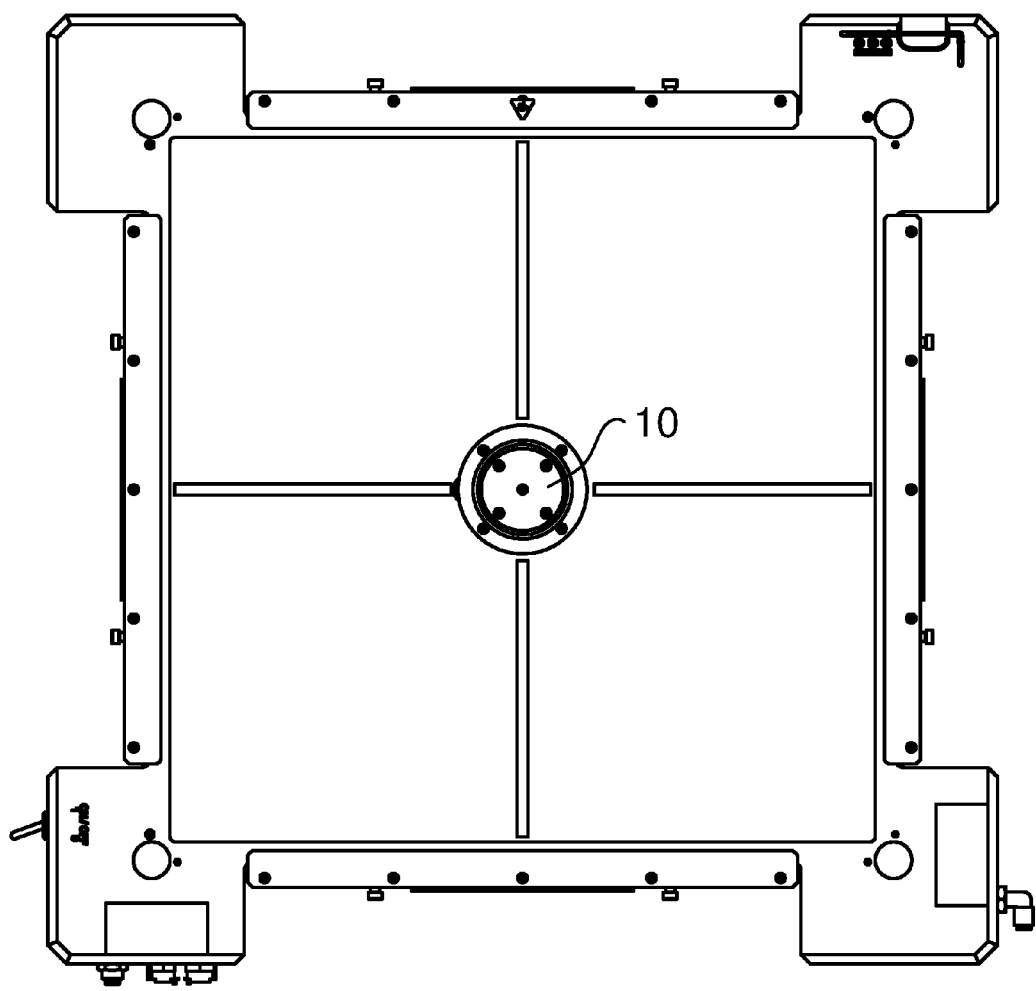
FIG. 5 shows the vacuum fixture of FIG. 1 mounted in the structure of FIG. 4.

The fixture 10 is mounted on a structure designed to support a large sample with minimum contact with the lower surface of the sample. Samples such as circuit boards may be damaged by contact, so they need to be supported with a rigid structure that assures a planar disposition of the sample while supporting it with as few contact points as possible. One such stage structure 40 is illustrated in FIG. 4. Four rigid beams 42 run between a fixture support well 44 and an outer frame 46. The beams are perfectly coplanar with the top surface of the frame to prevent downward bowing of the sample. Such four cross-beams, preferably cylindrical with a diameter of about 6 mm, have been found to be sufficient for that purpose while having only line contact with the underside of the sample. An underlying platform 48 provides a base where the well 44 is formed. The fixture 10 of the invention is mounted on the stage by placing it in the well 44, as illustrated in FIG. 5. In order to ensure that the fixture is also co-planar with the beams 42 and the outer frame 46, the well 44 is positioned lower, by an amount slightly greater than the thickness of the rim 14, so as to produce co-planarity of the piston 20 with the beams 42 in its retracted position (i.e., when under suction) while preventing any contact of the sample with the platform 48. Thus, as illustrated in the partially cut-out view of FIG. 6, when the fixture 10 is in place, the top of the piston 20 in its relaxed condition protrudes slightly higher than the beams 42 and frame 46 so as to enable contact with a sample S being measured.

Figure 6:
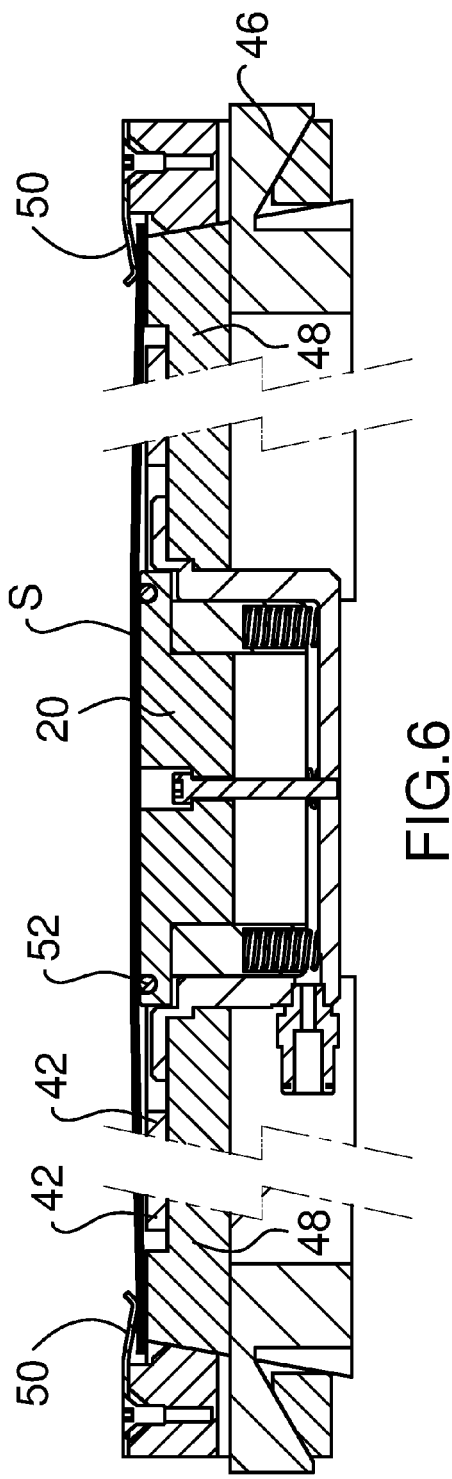
FIG. 6 is a partially cut-out, sectioned view of the fixture of FIG. 1 mounted in the structure of FIG. 4, including a sample clamped to the stage.
Figure 7:
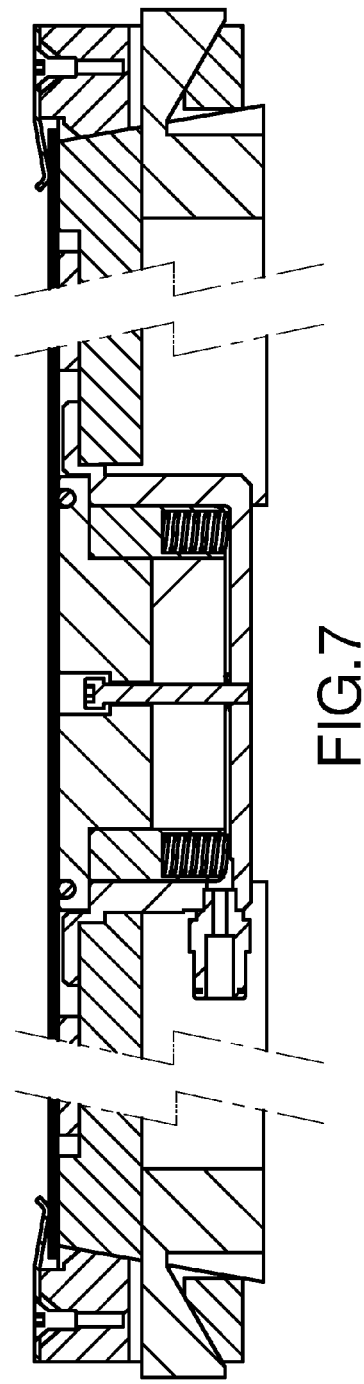
FIG. 7 is a view of FIG. 6 after the sample has been flattened by applying suction to the fixture of the invention.

In operation, the upwardly bowed sample S to be measured is placed on the stage structure 40 and secured by clamps 50 with the center of the sample resting on the top of the piston 20, as shown in FIG. 6. When vacuum is applied to the fixture, the suction is applied through the opening 38 draws the overlaying portion of the sample S toward the piston to form a seal. An O-ring 52 (see also FIG. 1) or another compliant sealing material may be provided to facilitate the formation of the seal, but the smooth surface of a Teflon® piston has been found to provide sufficient contact with the sample to effectively draw it in and seal the opening 39. Once this opening is sealed, the vacuum applied to the fixture becomes effective primarily in the interior 36 of the fixture and draws the piston 20 and the overlaying sample S all the way downward against the force of the springs 26 until the flange 22 is fully seated on the channel indentation 16 of the fixture's housing 12. At that point, the top of the piston 20 and the central portion of the sample S will be substantially coplanar with the beams 42, thus producing a flattened sample conforming to the coplanar support structure of the stage, as illustrated in FIG. 7.

Figure 9:
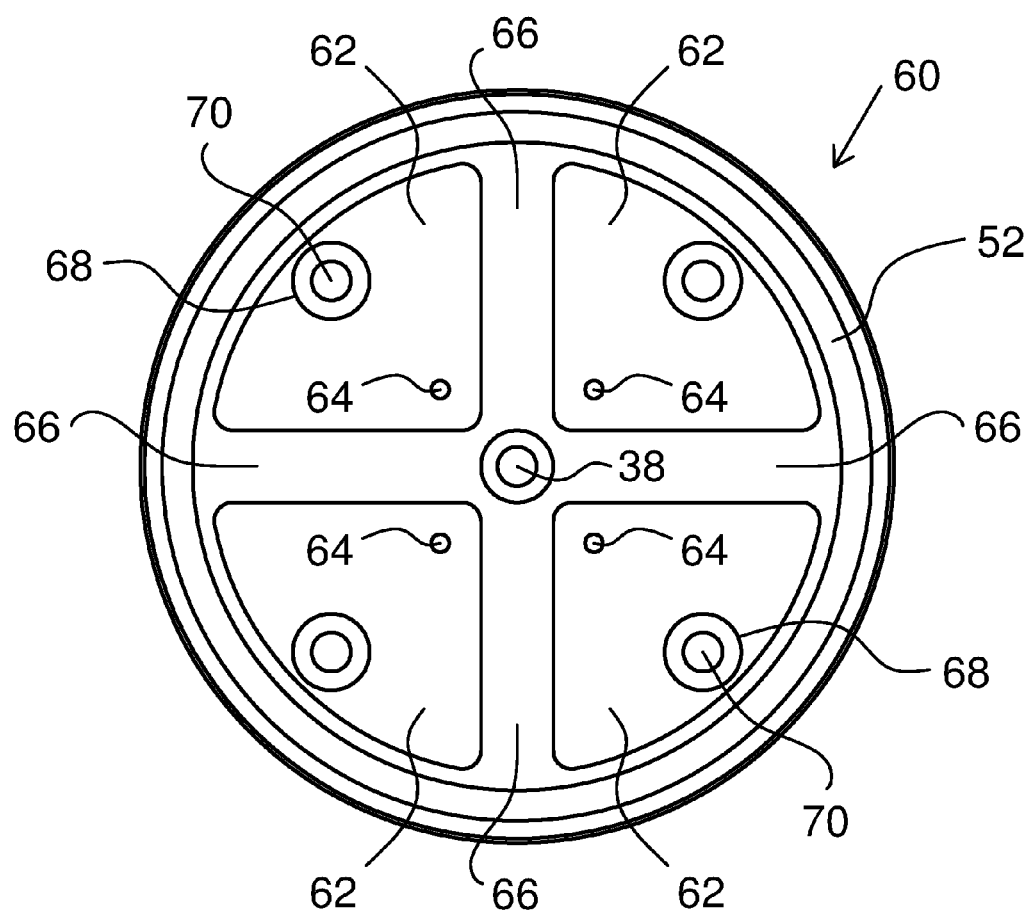
FIG. 9 is a top view of the piston of FIG. 8.
Figure 8:
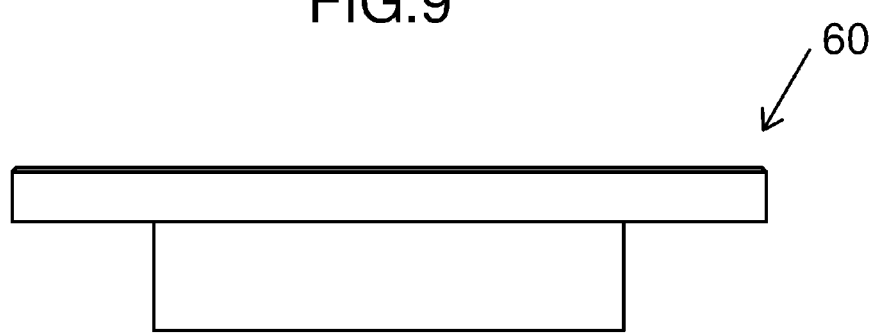
FIG. 8 is an elevational view of an alternative embodiment of the piston for the vacuum fixture of the invention.
Figure 10:
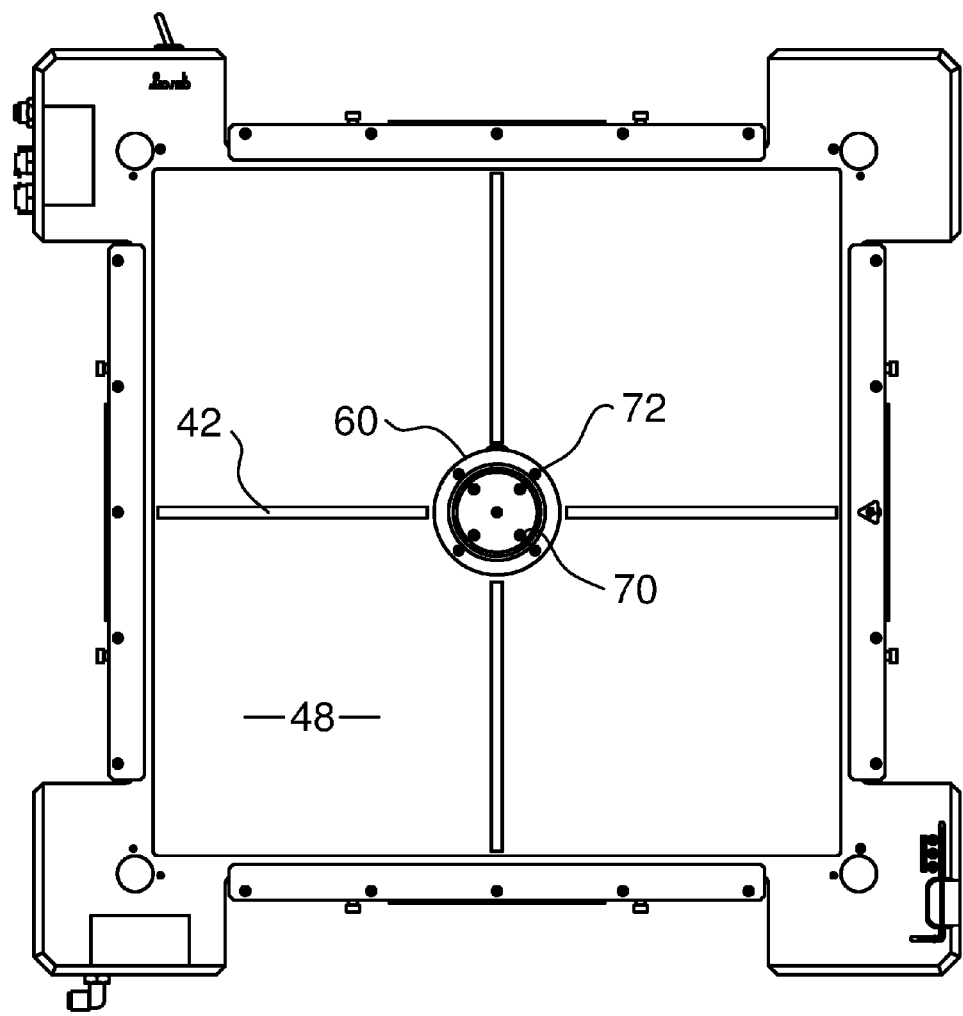
FIG. 10 illustrates the vacuum fixture of the invention with the piston of FIG. 9 mounted in the structure of FIG. 4.

A preferred alternative embodiment for the piston of the invention is shown in FIGS. 8 and 9. As seen in the elevational view of FIG. 8, the alternative piston 60 is essentially the same as the piston 20 described above. However, the top of the piston, shown in FIG. 9, is modified to further reduce the area of contact with the sample. Instead of relying only on the opening 39 to provide suction, the top surface of the piston 60 is modified by forming four recessed pockets 62 fluidly connected to the interior 36 of the fixture by means of respective perforations 64. As a result of the formation of the pockets 62, the only portions of the surface of the piston that contact the sample are the four ribs 66 produced by the modification. An O-ring 52 can still be used, if necessary, but it is not required for all samples. Additional through-openings 68 are provided, as in the case of piston 20, to attach the piston 60 to the underlying sleeve 24 with screws 70. FIG. 10 shows the modified fixture mounted on the support frame 46 of the stage. Additional screws 72 are preferably used to attached the fixture (10 or 60) to the platform 48 through apposite perforations in the flange 22.

In use, the vacuum fixture of the invention makes it possible to flatten an upwardly bowed, large, panel sample rapidly and with minimum sample contact by applying suction only to the center of the sample. A single vacuum source produces the dual action of adhering the actuating mechanism (the piston) to the sample and of retracting the piston to a position aligned with a coplanar support structure, thereby drawing in the center of the sample to flatten the panel. The invention enables the rapid flattening of a sample with the simple actuation of a vacuum-producing switch. No damage to the sample was experienced with operating pressures in the order of 0.7-0.9 bars, which, for example, were sufficient to flatten a 1-2 mm thick, 20-inch wide, circuit board in a matter of seconds by adhering its center to a 2-inch fixture as described above.

Thus, a vacuum mechanism has been described that greatly speeds up the process of measuring a sample with an optical instrument. As a result of its flattened condition, it becomes less likely that refocusing of the objective between measurements on different portions of the sample is necessary, thereby avoiding this time consuming part of large panel measurements.

As mentioned above, the invention has been described for simplicity in terms of an upward bowed panel and a suction mechanism (the fixture of the invention) placed below the center of the sample. However, it is understood that the same mechanism or a plurality of such mechanisms could be used in the same manner in order to flatten a panel with multiple bowed area. In such case, each mechanism would be placed substantially aligned with the approximate center of a bowed area so as to act specifically on that area. Similarly, one or more mechanisms could be used to flatten downward bowed spots in a sample by pulling down the edges of the sample against a support bearing approximately on the centers of the bowed areas. Such fixtures pulling down the edges of the sample could also be used to replace the clamps described above. Finally, the vacuum fixtures of the invention could be used not only to flatten a sample, but also to remove bulges so as to shape it to conform to a particular shape deemed optimal for a measurement.

Various changes in the details that have been described may be made by those skilled in the art within the principles and scope of the invention herein illustrated and defined in the appended claims. For example, the fixtures of the invention could be used to reduce vibrations in the sample during a measurement. Rather than for reshaping purposes, the vacuum force of the fixture would be used to keep the sample firmly in place. Thus, while the invention has been shown and described in what are believed to be the most practical and preferred embodiments, it is recognized that departures can be made therefrom within the scope of the invention, which is not to be limited to the details disclosed herein but is to be accorded the full scope of the claims so as to embrace any and all equivalent apparatus and methods.

What is claimed is:

1. A method for removing a bowed area from a panel sample, comprising the following steps:
   supporting the bowed area of the panel sample with support elements;
   providing a fixture with a movable component actuated by a vacuum source, the movable component having a top surface disposed above said support elements when no vacuum is applied and being drawn to a substantially coplanar position with said support elements when actuated by the vacuum source, said top surface being fluidly connected to the vacuum source and adapted to adhere to an overlaying surface of said bowed area of the panel sample when vacuum is applied; and
   operating said vacuum source to apply suction to said overlaying surface of the bowed area of the panel sample and to actuate the movable component to draw the bowed area to said substantially coplanar position with the support elements.

2. The method of claim 1, wherein said support elements include an outer frame and a plurality of coplanar beams, said outer frame including clamping means for retaining the panel sample during a measurement.

3. The method of claim 1, wherein said movable component is a piston slidably connected to a housing.

4. The method of claim 3, wherein said vacuum source is fluidly connected to the top surface of the piston through an interior compartment of the housing.

5. The method of claim 3, further including the step of urging said piston upward with a spring-loaded mechanism.

6. The method of claim 5, further including the step of limiting a maximum extension of said spring-loaded mechanism with a device coupled to the piston.

7. The method of claim 1, wherein said top surface of the movable component includes an O-ring.

8. The method of claim 1, wherein said top surface of the movable component includes a polytetrafluoroethylene material.

9. The method of claim 1, wherein said support elements comprise an outer frame and a plurality of coplanar beams, said outer frame including clamping means for retaining the panel sample during a measurement; said movable component is a piston slidably connected to a housing; said top surface of the piston includes a polytetrafluoroethylene material and an O-ring; said vacuum source is fluidly connected to the top surface of the piston through an interior compartment of the housing; and the method further includes the steps of urging the piston upward with a spring-loaded mechanism and of limiting a maximum extension of the spring-loaded mechanism with a device coupled to the piston.

* * * * *